United States Patent [19]

John

[11] 4,417,592
[45] Nov. 29, 1983

[54] DIGITAL ELECTROENCEPHALOGRAPHIC INSTRUMENT AND METHOD

[76] Inventor: E. Roy John, 930 Greacen La., Mamaroneck, N.Y. 10546

[21] Appl. No.: 262,395

[22] Filed: May 11, 1981

[51] Int. Cl.$^3$ .............................................. A61B 5/04
[52] U.S. Cl. ................................ 128/731; 346/33 ME
[58] Field of Search ................................ 128/731–732, 128/733, 710, 712; 346/33 ME

[56] References Cited

U.S. PATENT DOCUMENTS

| | | | |
|---|---|---|---|
| 3,621,836 | 11/1971 | Nagatomi | 128/731 |
| 3,623,477 | 11/1971 | Trent | 128/731 |
| 3,809,069 | 5/1974 | Bennett | 128/731 |
| 3,848,586 | 11/1974 | Suzuki et al. | 128/731 X |
| 4,171,696 | 10/1979 | John | 128/731 |
| 4,188,956 | 2/1980 | John | 128/731 |
| 4,201,224 | 5/1980 | John | 128/731 |
| 4,323,079 | 4/1982 | Demetrescu | 128/731 |

*Primary Examiner*—Lee S. Cohen
*Assistant Examiner*—Angela D. Sykes
*Attorney, Agent, or Firm*—Eliot S. Gerber

[57] ABSTRACT

An electroencephalographic (EEG) system includes an electroencephalographic instrument comprising a plurality of electrodes adapted to be removably connected to the patient's head to detect brain waves; a plurality of amplifiers, with each amplifier connected to a pair of electrodes; an output multiplexer and a multi-line electrographic recording device, such as a matrix printer, whose display is an on-line display of multi-channel simultaneous wavy lines on a recording medium, such as a strip chart. A digital signal conditioning system is connected between the outputs of the amplifiers and the input of the recording device and functions to minimize misleading effects of muscular artifacts, to detect epileptiform spikes and sharp waves, and to perform quantitative analysis of the EEG signals. This signal conditioning system includes a comparison means which compares analytical features of the patient's brain waves on a statistical basis, with norms stored in a digital storage means. These features are extracted from the EEG by spectral analysis, coherence analysis and symmetry analysis. Other modular digital systems and software may be added to compute cortical and brainstem average evoked potentials using multimodal sensory stimuli, to extract diagnostic features from the average evoked potentials (EP's) by computing algorithms, to construct graphic and alphanumeric displays, or to write an analytic diagnostic report.

12 Claims, 1 Drawing Figure

DIGITAL ELECTROENCEPHALOGRAPHIC INSTRUMENT AND METHOD

BACKGROUND OF THE INVENTION

The present invention relates to medical instruments and methods and more particularly to an improved system and method in electroencephalography.

At the present time the most widely used instrument in electroencephalography is an analog system which amplifies and records the patient's brain waves. The system generally comprises a plurality of electrodes which are adapted to be connected to the patient's head, a set of amplifiers with each amplifier connected to a pair of electrodes, one of the pair generally being a reference electrode, and a multi-channel electrographic recording instrument connected to the amplifiers. Each channel of the recording instrument records a wavy line representing the patient's brain waves at the electrode corresponding to the channel input. For example, an ink pen of a galvanometer type recorder may record a wavy mark on a moving sheet of paper. The recorded set of waves is visually examined by a neurologist who, on the basis of his training and experience, will determine if there are any abnormalities. Neurologists, it is believed, would prefer to work with such recorded sets of waves for visual analysis since their parameters have been well documented and their major features known to them. Such major features include the frequency of the waves, their amplitude, the brain region (channel), waveform peculiarities, interhemispheric coherence, duration and envelope of recurring series of waves, voltage-frequency relationships and reactivity.

The present analog system suffers from a number of problems. The brain wave is a very faint electrical signal and it is easily drowned out by electrical signals arising from voluntary and involuntary muscle movement (muscle artifact). For example, the patient's eyelids may flutter and the electrical signals from such fluttering motion may obscure the patient's brain waves. It may be difficult, even for a highly trained neurologist, to visually distinguish a recording of muscle artifact from the recording of a patient's brain waves. In uncooperative patients, the bulk of the recorded material may consist of artifacts.

Another problem arises from patients' production of spikes and sharp waves, which may be the type of wave associated with epileptic activity. Although these sharp waves may be seen visually on a recording, it may be difficult at times to distinguish them from muscle artifact, sharp alpha waves and pulse rhythm. This distinction often depends on the context of the background activity in which they appear. In addition, the neurologist may wish to know the frequency of occurrence of such sharp waves over a period of time, and constructing an exhaustive inventory of such events is, by visual inspection, difficult and tedious.

In the inventor's U.S. Pat. No. 4,171,696, entitled "Prevention of Distortion of Brainwave Data Due To Eye Movement Or Other Artifacts," incorporated by reference herein, a system and method for limiting the adverse effects of muscle artifact is described. The system includes trans-orbital electrodes, a digital computer and a multi-channel recorder. Certain articles and patents relating to the problem of artifact compensation in electroencephalography are discussed in the U.S. Pat. No. 4,171,696, see column 1, line 46, through column 2, line 47.

The inventor, in his text "Neurometrics: Clinical Applications of Quantitative Electrophysiology, Functional Neuroscience, Vol. II" (Erlbaum Assoc. 1977), page 78, incorporated by reference herein, discusses reduction of the adverse effects of muscle artifact on brain wave detection in the context of a large digital computer based system. That system provided for the monitoring of eye movement and accelerometer channels, the accelerometer being attached to the patient's head. A threshold maximum amplitude value is set. First and second derivatives of the brainwaves are computed and evaluated relative to other threshold criteria. If artifact was detected, either the recording was marked or that portion rejected.

In U.S. Pat. No. 3,848,586 entitled "Signal Detection System," issued Nov. 19, 1974 to Suzuki et al, a signal detection system is described for use in an EEG instrument to reduce noise. The Suzuki et al patent points out that the prior art noise reduction method using analog low-pass filters were deficient because (i) the filter system attenuated high frequency components such as spike waves; and (ii) the filter system may product an artificial wave which becomes mixed with the brain wave signals. Suzuki et al sought to reduce noise due to muscle action (muscle artifact) by an analog-to-digital conversion of the brain waves, stretching the time axis, digital-to-analog conversion, and a recording using a pen recorder. In Suzuki et al waveforms witth a gradient steeper than a predetermined value (threshold $C_1$) are removed by correcting them with a predetermined voltage ($C_2$). The predetermined value selections are based on the patentee's theory that muscle artifact signals, compared to shapr waves, have a steeper gradient and a short duration.

Objectives and Features of the Invention

It is an objective of the present invention to provide a method and system in electroencephalography which will provide an "on-line" analysis the patient's brain waves and display the analyzed brain waves in the form of a plurality of wavy lines similar in appearance to the wavy lines produced by conventional analog instruments.

It is an objective of the present invention to provide such a method and system which includes a multi-line recorder and a digital signal conditioning means used to discriminate between the patient's muscle artifact and brain waves.

It is a further objective of the present invention to provide such a method and system in which the digital signal conditioning means also provides an analysis of the patient's brain waves compared to norms held in digital storage means.

It is a further objective of the present invention to provide such a method and system which also provides a multimodal sensory stimulator, and a program controlling the stimulator, so that the patient's evoked potentials (EPs) may be obtained and compared with norms stored in the digital storage means.

It is a still further objective of the present invention to provide a method and system in electroencephalography in which the instrument would, at least in its input controls and the appearance of its outpput, be familiar to users of conventional analog EEG machines, and yet which includes signal conditioning means using digital techniques in order to detect and lessen the adverse effect of muscle artifact on the brain wave recording, and to perform quantitative analyses of the signals.

It is a feature of the present invention to provide an electroencephalographic system which includes a digital EEG instrument including (a) a plurality of electrodes adapted to be removably attached to the head of a patient to detect the brain waves of the patient; (b) a plurality of amplifiers each connected to a different pair of electrodes; and (c) a digital electrographic multi-line recording device such as a digital matrix printer providing graphic outputs. Each of the amplifier channels provides input to signal conditioning and analytical software, which constructs an output as a temporal sequence of events constituting a channel in the multi-channel display produced by the recording device.

An improvement of the present invention is the utilization, in such an EEG system, of a digital signal conditioning and quantitative analysis system connected between the amplifiers and the multi-line recording device. The digital signal conditioning system includes A/D means to convert the analog signals from each of the amplifiers into digital signals representing samples of the patient's brain waves.

The A/D converter means may be a variable gain multiplexed analog-digital converter. The digital signal conditioning and quantitative analysis system also includes digital data storage means and digital comparison means to compare quantitative features extracted from the brain waves with comparable brain wave norms in the data storage.

The comparison means includes means to compare the samples of the patient's brain waves with norms for the amplitude, frequency composition, coherence and symmetry of the sample stored in the storage means, means to detect the samples representing brain wave amplitude at a selected level above the norm, means to detect the samples representing brain wave amplitudes at a selected level below the norm, and means to analyze the samples for spikes and sharp waves.

The electroencephalographic system of the present invention includes digital signal conditioning means. After processing, the digital signals are sent to a multiplexer switch which connects them, in rapid sequence, to the recorder for each of the channels. Artifact-free analog brain waves and the spikes and sharp waves are recorded apparently simultaneously and "on line" by the recorder. The recorder is a multi-channel matrix recorder.

It is also a feature of the present invention to provide such an electroencephalographic system and method in which additional electrodes are connected to the patient's temporal muscle and neck muscles for artifact detection. Amplifiers are connected to the temporal and neck electrodes and means connect the amplifiers to the A/D means so that electro-oculograms (EOG) and electromyograms (EMG) of the patient are detected and analyzed.

The above-described digital analysis system may by considered one module of an optional multi-module system. An additional and optional module includes means for the spectral analysis, coherence analysis and symmetry analysis of the patient's brain waves; means for the Z-transforms of the analysis compared to stored means; means to automatically generate a report and an evoked potential module unit.

BRIEF DESCRIPTION OF THE DRAWINGS

Other objectives and features of the present invention will be apparent from the following detailed description of the invention which should be taken in conjunction with the accompanying drawings.

In the drawings.

DETAILED DESCRIPTION OF THE INVENTION

Figure 1:
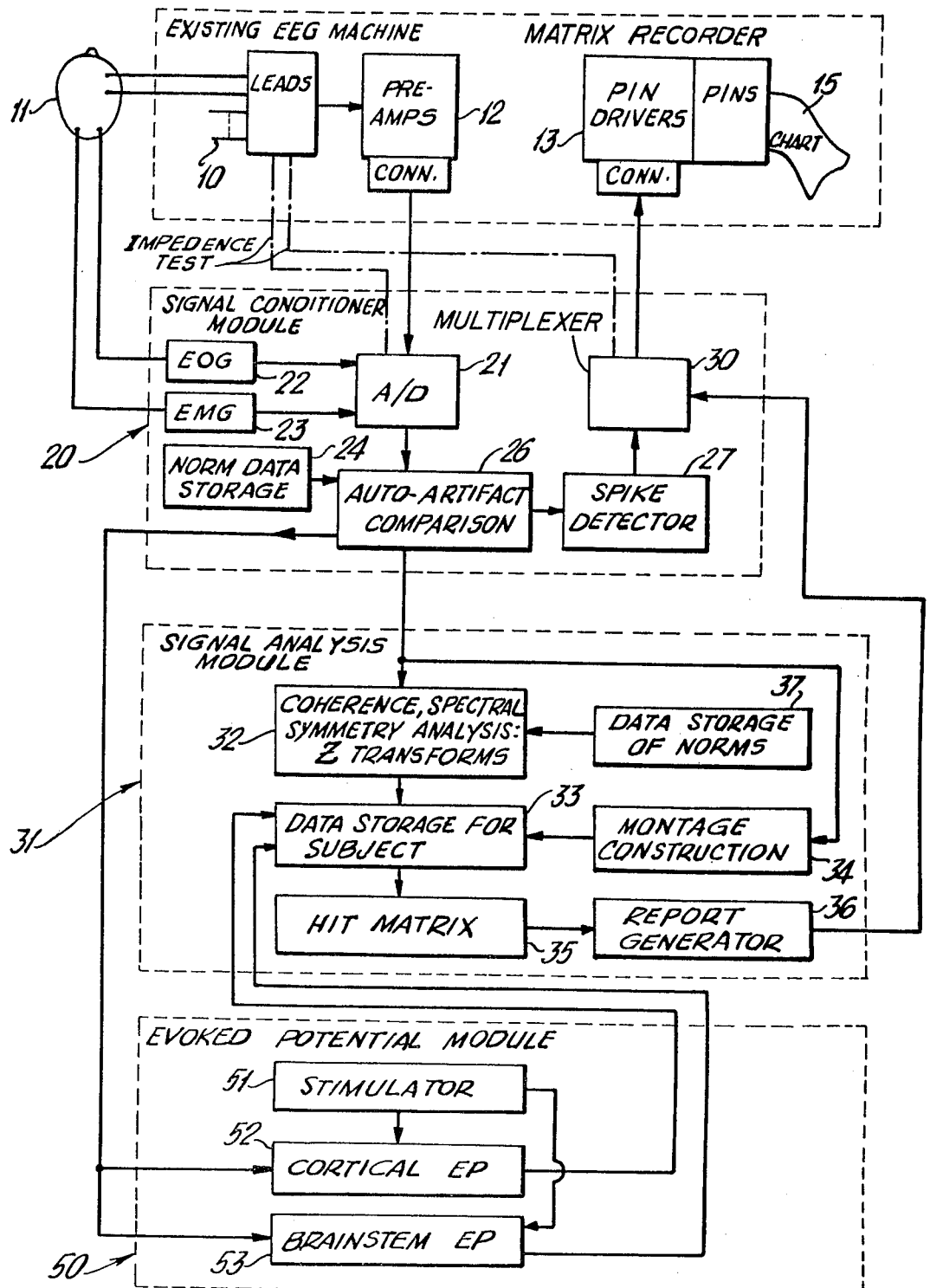
FIG. 1 is a block schematic diagram of the system of the present invention.

A portion of the electroencephalography (EEG) instrument shown as part of the system of FIG. 1 is marked "Basic EEG Machine." As shown, the Basic EEG Machine has a plurality, usually twenty, of electrode leads 10, each of which is removably connectable to the head of the patient 11, although only a few of such leads are illustrated for the purpose of clarity of the drawing. Each of the leads 10 is connected to the input of a respective amplifier 12 ("pre-amps").

The matrix recorder 13 is sometimes called an electrostatic printer or a matrix printer, see Dessauer & Clark, "Xerography & Related Processes," pages 439-449 (Focal Press 1965). In one type of matrix recorder latent electrostatic charge patterns are formed by selectively energizing pin electrodes in a print head mounted 3-35 thousandths of an inch from a dielectric recording medium. The pins are energized with an electrical pulse which produces an electrical discharge and creates negative ions which are accelerated toward the recording medium by the electric field. They accumulate on the recording medium to form a pattern of dots consisting of negative ions, which constitutes a latent image of the desired line or alphanumeric character.

The recording medium, such as chart 15, consists of a base paper which is electrically conductive and coated with a dielectric plastic having a high resistivity. As the negative ions accumulate on the top surface of the plastic coating, electrons at the paper-plastic interface flow away through the conductive paper to the base electrode and finally back to the print head through the pulse circuitry and the induced positive charge at the paper-plastic interface creates a strong electric field through the plastic coating. The charges form a latent electrostatic charge pattern which may be developed using xerographic developing systems.

An alternative type of matrix recorder uses a modified cathode ray tube as a high-speed switch to selectively charge electrically isolated pins of a tightly spaced pin matrix which is positioned in the face of the tube. Charge transfer takes place between the ends of the pins and a closely positioned moving web of coated paper. The face of the cathode ray tube is generally constructed with a single row of fine wires or pins which penetrate the tube face and permit the beam current to pass through the tube envelope. The length of the row of pins is equal to the width of the recording paper.

In both types of matrix recorders the latent electrostatic image can be developed subsequently with xerographic techniques and fuzed to provide a permanent hard copy.

Brain waves typically are in the range of 50-300 milliseconds in duration. Such a wave can be satisfactorily visualized on a recording medium, such as paper strip chart 15, if it is composed of 20-100 individual dots. If the wave is rapid, for example, 50 milliseconds, and the dot density high, for example, 100 dots, then each dot would be ½ milliseconds, i.e., 500 microseconds. If the multiplexer 30 connected to the matrix recorder 13 has 20 output channels, then it may scan at a range of 500/20 or 25 microseconds a channel.

To the human eye it appears that each wavy line on the chart 15 is being printed by a continuous sequence of dots. Actually, the discharge control to the matrix pins of the matrix recorder 13 is established by the output multiplexer 30 so that only one dot is printed in each channel and then, under switching control from the multiplexer 30, a dot is printed in the next wavy line. The wavy lines produced on chart 15 are "on-line" in the sense that the wavy lines, to the human interpreter, appear simultaneously with the brain waves they represent.

The signal conditioner module 20 is placed in a series between the amplifiers 12 and the matrix recorder 13. As illustrated in FIG. 1, the signal conditioner module 20 includes an analog-to-digital converter 21 (A/D converter 21) which is a variable gain and multiplexed A/D converter. For example, A/D converter 21 is an 8-bit converter having a sample rate of 100 per second.

An EOG amplifier 22 has leads connected to the patient to provide an electro-oculogram (EOG) output, indicating eye movements. Similarly the EMG amplifier 23 is connected by leads to the patient to provide an electromyogram (EMG) of the temporal and neck muscles.

The A/D converter 21 is connected to the auto-artifact comparison means 26.

The auto-artifact comparison means 26 performs signal conditioning to provide artifact-free spike-marked segments. Those segments are converted to voltage fluctuations and plotted by the matrix recorder 13.

The auto-artifact means 26 utilizes the memory and processing capability of a suitable digital computer, preferably a micro-processor, such as an LSI microprocessor of the 11/03-11/23 type. The auto-artifact means 26 is connected to the spike detector 27 whose output is to a multiplexer 30. The auto-artifact means 26 indicates that the brain waves are artifact-free and that information is transmitted to the spike detector means 27. Under control of auto-artifact means 26, only those brain wave signals which are artifact-free are sent to the recorder 13.

In operation, the signals representing segments of EEG, EOG and EMG, each of 2.5 seconds in duration, are examined in sequence, for example, at a sample rate of 140 Hz. The auto-artifact comparison means 26, using a stored program control, performs an analysis of the digitized EEG, EOG and EMG signals. That analysis includes, for each channel of EEG, i.e., for each of the twenty channels, the following procedures:

(i) The amplitude spectrum of each segment is examined;

(ii) Mean values and standard deviations of absolute amplitude are computed and the distribution of values in each segment are examined.

A segment is accepted as being artifact-free, i.e., valid data, if the distribution of values in each segment (from an EEG channel) is random (Gaussian), and if the absolute amplitudes from that segment do not exceed a specified selected threshold. The segment is suspected of being contaminated with artifact if the distribution of mean-values and standard deviations for its channel and for the segment includes voltages whose amplitudes exceed a selected threshold. The selected threshold for each channel may be separately chosen.

If the voltage amplitudes are all below the selected voltage amplitude threshold (artifact threshold) but the distribution is statistically significant (non-Gaussian, i.e., non-random), the segment is considered to (a) contain artifact, or (b) contain a paroxysmal discharge (a sharp wave).

The following procedure discriminates between artifacts and paroxysmal discharges. The statistically significant and below-threshold (non-random) segments are each examined by a sharp wave detection process in sharp wave detector means 27. If a paroxysmal discharge, such as an epileptic spike, is not detected, the segment is rejected as being contaminated by artifact. If events within any segment appear to be a paroxysmal discharge (satisfy the sharp wave detecting process), then the segment is examined for other similar events (satisfying the sharp wave detecting process) occurring within 200 milliseconds. If such similar events are found, the segment will be rejected as being contaminated by muscle artifact. In other words, paroxysmal discharges must be spaced in time. If no additional sharp events are found within that 200 millisecond interval, the data will be accepted as valid EEG data which contains a sharp wave. Optionally, the rejected segments may be marked and the presence of artifact indicated by an appropriate marker on the time base of the recording.

The paroxysmal discharges (sharp waves) are found by analysis of the brain waves from each channel to determine their mean amplitude and their first ($dV/dT$) and second ($d^2V/dT^2$) derivates. In general, sharp waves are electrical excursions 20 to 80 MS in duration which exceed predetermined limits of rise, for example (2 $\mu V/mS$), amplitude (50 $\mu V$), fall (2 $\mu V/MS$) and sharpness [$d^2V/dT^2$) $\mu/0°$] and which may occur in each electrode channel. These are possible epileptiform spikes. Sharp waves are defined in mathematical terms as $A > M_A + 3\sigma_A$ for 20 MS < "sharp wave" < 80 MS, $dV/dt > Mv'/dt + 3\sigma_{v'}$ or 2 $\mu v/MS$, $d^2V/dt^2 > M_{v''} + 3\sigma_{v''}$ or < 10°. No true sharp wave can occur within 200 MS of any other sharp wave, and this condition is included in the definition. In these formulas $dv/dt = v'$, $d^2V/dt^2 = v''$.

All valid segments are plotted on the chart or other "hard copy" display (hereinafter called "display copy"), with any sharp waves indicated by underlining or by an appropriate mark correlated with the time base indication on the display. Such sharp waves may be collected and displayed separately for each channel.

The microprocessor automatically calibrates each channel and automatically performs iterated tests of the impedance of each electrode before and during each recording. At the end of the recording session, the total number of sharp waves detected in each channel are indicated on the display copy. For example, the number is indicated by numeric entries.

The signal analysis module 31 is an optional module which may, if desired, be added to the system comprising the basic EEG machine and the signal conditioning module 20. The signal analysis module 31 operates on digital data, representing the subject's brain waves, which is artifact-free. The amount of data handled by the signal analysis module 31 requires that its hardware consist of additional digital data memory, preferably a dual-density floppy disk drive and its controller.

The various blocks of FIG. 1 illustrate the functions performed by the signal analysis module 31; those functions are performed by its processing of the digital data received from the auto-artifact comparison 26. That processing of the data is by the "software," i.e., the replaceable memory, which is found on the floppy disks or other form of data memory.

The first function is to perform coherence, spectral symmetry analysis and Z-transforms 32. Such analysis is performed by comparing the subject's brain waves with the norms stored in the data storage of norms 37 (data memory), the norms being based upon data collected from a statistically meaningful set of subjects, as explained in the inventor's prior U.S. Pat. No. 4,201,224 entitled "Electroencephalographic Method and System For The Quantitative Description of Patient Brain States," incorporated by reference herein, at column 7, line 63-column 8, line 36. A "hit matrix" 35 is an imaginary chart having columns listing each electrode lead and rows listing each of the extracted quantitative features, for example, coherence. The hit matrix determines if the subject's data, for each electrode lead and for each quantitative measure, is "abnormal", i.e., outside the range of the norms established in the data memory 37.

The report generator 36, based upon the data information of the hit matrix, will generate a report which will be displayed on the chart 15. Preferably the report, in humanly readable language, explains (i) the location of the abnormality on the "hit matrix," i.e., which electrode lead and which quantitative test; (ii) how far it differs from the norm, i.e., its severity; and (iii) what are the likely and possible causes and implications of the specific abnormality. The language giving these explanations for each area (row and column) of the hit matrix is provided by the data storage 37.

In addition, as the data from each electrode lead are stored in data storage for subject 33, it is possible to construct bipolar or multiple electrode montages. A suitable method for the construction of such montages is given in the inventor's prior U.S. patent application Ser. No. 873,118, filed Jan. 30, 1978, entitled "System and Method For Electrode Pair Derivations in Electroencephalography," incorporated by reference herein. The montage construction 34 is communicated to the data storage for subject 33 and then to the hit matrix 35 and becomes part of the report which is automatically generated by report generator 36 for those montages which are abnormal.

The evoked potential module 50, which is an optional module which may be added to the system, includes as its only additional hardware a stimulator 51. The stimulator 51 preferably provides visual stimulation, such as a flashable light; auditory stimulation, such as click noises; and somatosensory stimulation, such as a slight shock. Each stimulation may be controlled so that it is to the right or left eye, ear or median nerve. The stimulator 51 is preferably controlled under program control by the microprocessor and its program may be taken from storage in its floppy disk storage, see the inventor's prior U.S. Pat. No. 4,201,224, identified above, at column 5, line 65-column 6, line 9. The artifact-free data from the auto-artifact comparison 26 is analyzed into "cortical EP" 52 (evoked potential from the cortical region of the brain associated with long latency near-field) and "brainstem EP" 53 (evoked potential from the brainstem region associated with short latency far-field).

The description given above of the various optional modules constituting the system of the present invention is intended as a guide for a suitable system based upon the experiments that have been conducted. However, it will be understood that, as improvements are made in the various system components and devices, they may be incorporated in the system within the scope of the present invention. Various elements of the system, for example, data analysis and reduction methods, and further details concerning other elements of the system, may be found in the inventor's patents and pending patent applications referred to above.

What is claimed is:

1. An electroencephalographic system for the on-line conditioning of signals representing brain waves and representing muscle artifact, comprising a plurality of electrodes adapted to be removably attached to the head of a patient, a plurality of amplifiers each connected to a different pair of said electrodes, a matrix multi-channel display and recorder which in response to digital signals displays a copy of a plurality of the brain wave signals simultaneously in the form of a plurality of visible wavy lines on a recording surface, each wavy line being a series of dots which is the record of a different pair of said electrodes;

a digital signal conditioning means connected between said amplifiers and said multi-line channel dispay and recorder to reduce the adverse effects of said muscle artifact signals, said digital signal conditioning means including:

A/D means to convert the analog signals from each of said amplifiers into digital signals representing samples of the patient's brain waves;

digital data storage means for the containing of brain wave norms;

digital comparison means to compare said brain waves with brain wave norms in said data storage means;

said comparison means including means to compare the samples of the patient's brain waves with a norm for the amplitude of the sample stored in said storage means, means to detect said samples representing brain waves at a selected level above said norm, means to detect said samples representing brain waves at a selected level below said norm and means to analyze said samples for spikes and sharp waves;

connection means to connect said A/D means, digital data storage means and comparison means to provide said signal conditioning;

multiplexer means connected to said digital signal conditioning means and said recorder to distribute digital data from said digital signal conditioning means to the various channels of the recorder so that artifact-free brain waves and the said spikes and sharp waves are recorded by said recorder.

2. An electroencephalographic system as in claim 1 wherein the A/D means is a variable gain multiplexed analog-digital converter.

3. An electroencephalographic system as in claim 1 and further including electrodes adapted to be connected to the patent's temporal muscle and neck muscles for artifact detection; electro-oculogram (EOG) and electro-myogram (EMG) detectors and amplifiers connected to said temporal and neck electrodes for producing the electro-oculograms and electro-myograms of the patient; means connecting said EOG and EMG amplifiers to said A/D means; and means to detect and analyze the said electro-oculograms (EOG) and electromyograms (EMG) of the patient.

4. An electroencephalographic system as in claim 1 and further including, as an additional portion of said conditioning means:
   means to generate the spectral analysis, coherence analysis and symmetry analysis of the said brain waves; and
   means for computing the Z-transforms of the said spectral, coherence and symmetry analysis compared to stored norms.

5. An electroencephalographic system as in claim 4 and further including:
   means to automatically generate a report stating said Z-transforms.

6. An electroencephalographic system as in claim 1 wherein said data storage means includes magnetic floppy disks.

7. A method in electroencephalography for the on-line conditioning of signals representing brain waves, including the steps of removably attaching a plurality of electrodes to the head of a patient to detect signals representing the brain waves and muscle artifact of the patient, connecting a plurality of amplifiers with each amplifier being connected to a different pair of said electrodes, producing an on-line copy of the brain wave signals on a matrix multi-channel display and recorder which is responsive to digital signals, the display of the brain wave signals from each different pair of the said electrodes being a visible wavy line composed of a series of dots and being simultaneously displayed and recorded with the brain wave signals from other pairs of said electrodes;
   comprising connecting a means for digital signal conditioning between said amplifiers and said recorder said means reducing the adverse effects of said muscle artifact signals said digital signal conditioning including:
   converting the analog signals from each of said amplifiers into digital signals representing samples of the patient's brain waves using A/D means;
   storing brain wave norms in a digital data storage means; and
   comparing said brain waves with brain wave norms in said data storage means using digital comparison means;
   said comparing including comparing the samples of the patient's brain waves with a norm for the amplitude of the sample stored in said storage means, detecting said samples representing brain waves at a selected level above said norm, detecting said samples representing brain waves at a selected level below said norm and analyzing said samples for spikes and sharp waves; and
   connecting multiplexer means to said digital signal conditioning means and said recorder and distributing digital data from said digital signal conditioning means to the various channels of the recorder so that artifact-free brain waves and the said spikes and sharp waves re recorded by said recorder.

8. An electroencephalographic method as in claim 7 wherein the said conversion into digital signals is accomplished by varying the gain of a multiplexed analog-digital converter.

9. An electroencephalographic method as in claim 7 and further including attaching electrodes to the patient's temporal muscle and neck muscles for artifact detection; connecting EOG and EMG amplifiers to said temporal and neck electrodes to produce electro-oculograms (EOG) and electromyograms (EMG) of the patient; connecting analysis means to said EOG and EMG amplifiers to detect and analyze the said electro-oculograms (EOG) and electromyograms (EMG) and displaying said EOG and EMG analysis on said matrix display.

10. An electroencephalographic method as in claim 9 and further including, as an additional step of said signal conditioning;
    performing spectral, coherence and symmetry analysis on the basis of comparisons to said stored norms, and generating the Z-transforms of the said spectral, coherence and symmetry analysis.

11. An electroencephalographic method as in claim 10 and further including the step of:
    automatically generating a report stating said Z-transforms.

12. An electroencephalographic method as in claim 7 wherein said storing is by data input onto flopy disks.

* * * * *